United States Patent [19]
Cohen et al.

[11] Patent Number: 5,795,904
[45] Date of Patent: Aug. 18, 1998

[54] ENHANCED FUNCTIONAL RECOVERY OF THE HEART BY LOSARTAN TREATMENT AFTER AN ISCHEMIC ATTACH

[75] Inventors: Sheila M. Cohen, Cranford; Jeffrey G. Werrmann, Pittstown, both of N.J.

[73] Assignee: Merck & Co., Inc., Rahway, N.J.

[21] Appl. No.: 761,261

[22] Filed: Dec. 6, 1996

[51] Int. Cl.$^6$ .................................................. A61K 31/41
[52] U.S. Cl. .................................................. 514/381
[58] Field of Search .................................................. 514/381

[56] References Cited

U.S. PATENT DOCUMENTS

| | | |
|---|---|---|
| 5,538,991 | 7/1996 | Ashton et al. ............................ 514/397 |
| 5,565,485 | 10/1996 | Bagley et al. ............................ 514/452 |

OTHER PUBLICATIONS

Thomas et al, CA 125: 238142, 1996.
Fleetwood, G., eta l., "Involvement of the Renin–Angiotension System in Ischemic Damage and Reperfusion Arrhythmias in the Isolated Perfused Rat Heart", J. of Cardio. Pharm., vol. 17, pp. 351–356, 1991.

Yoshiyama, M., et al., "Cardioprotective Effect of the Angiotension II Type 1 Receptor Antagonist TCV–116 on Ischemia–Reperfusion Injury", Clinical Investigations, vol. 128(1), pp. 1–6, 1994.

Werrmann, J.G. et al. "Comparison of Effects of Angiotensin–Converting Enzyme Inhibition with those of Angiotensin II Receptor Antagonism on Functional and Metabolic Recovery in Postischemic Working Rat Heart as Studied by |31P| Nuclear Magnetic Resonance", J. of Cardio. Pharm., vol. 24, pp. 573–586, 1994.

*Primary Examiner*—Rebecca Cook
*Attorney, Agent, or Firm*—Valerie J. Camara; Mark R. Daniel

[57] ABSTRACT

Losartan, its active metabolite, EXP3174, or the pharmaceutically acceptable salts of these compounds for use in enhancing the functional recovery of the heart after an ischemic attack.

5 Claims, 4 Drawing Sheets

| BASELINE WORKING-HEART PERFUSION (30 MIN) | GLOBAL ISCHEMIA AT 36.2 ±0.2° C (20 MIN) | LANGENDORFF-MODE REPERFUSION (12 MIN) | WORKING-HEART REPERFUSION CONSTANT AFTERLOAD (35 MIN) | WORKING-HEART REPERFUSION CONSTANT MAP (5-10 MIN) |

THE PERFUSION PROTOCOL

FIG.1

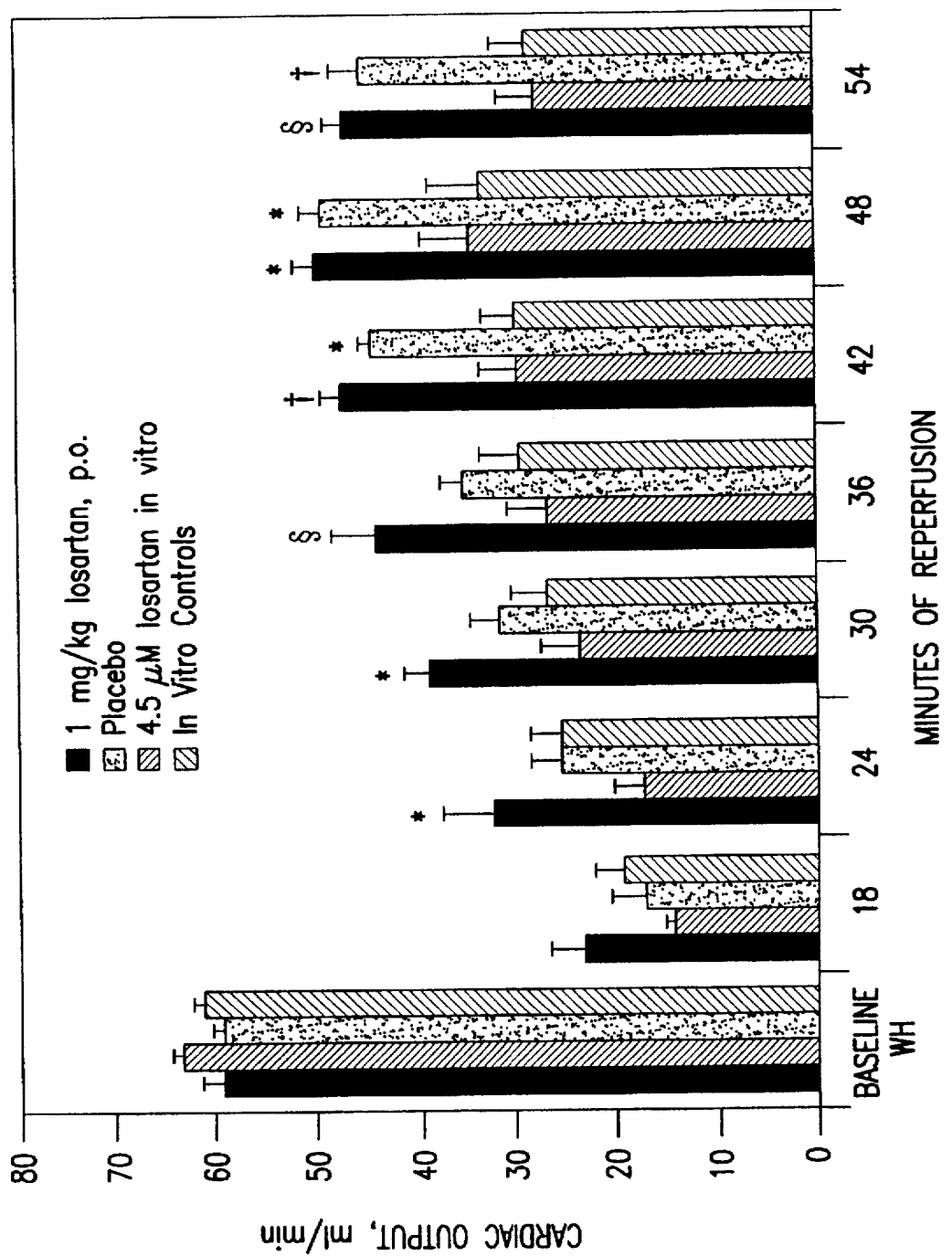

ENHANCED FUNCTIONAL RECOVERY OF THE HEART BY LOSARTAN TREATMENT AFTER AN ISCHEMIC ATTACH

BACKGROUND OF THE INVENTION

The discovery of orally active, nonpeptide angiotensin II (AII) receptor antagonists [See Wong, P. C., et al., "Nonpeptide Angiotensin II Receptor Antagonists, IV EXP6155 and EXP6803", *Hypertension* 1989, Vol. 13, pp. 489–97] has provided important new tools to help decipher the complex role of the renin-angiotensin system in the development of myocardial dysfunction during ischemia and subsequent reperfusion. The identification and classification of two AII receptor subtypes $AT_1$ and $AT_2$ were early results of this discovery [See a) Blankley, C. J., et al., "Synthesis and Structure-activity Relationships of a Novel Series of Nonpeptide Angiotensin II Receptor Binding Inhibitors Specific for the AT-2 Subtype", *J. Med. Chem.*, 1991, Vol. 34, pp. 3248–60; b) Chang, R. S. L., et al., "Angiotensin Receptor Subtypes in Rat, Rabbit and Monkey Tissues: Relative Distribution and Species Dependency", *Life Sci.*, 1991, Vol. 49, pp. 1485–90; and c) Hodges, J. C., et al., "Angiotensin II Receptor Binding Inhibitors", *Drug Fut.*, 1992, Vol. 17, pp. 575–93]. Treatment with the AII $AT_1$ receptor antagonist losartan following myocardial infarction (MI) has been reported to improve cardiac pump performance [See a) Raya, T. E. et al., "Hemodynamic Effects of Direct Angiotensin II Blockade Compared to Converting Enzyme Inhibition in Rat Model of Heart Failure", *Am. J. Hypertens.*, 1991, Vol. 4, pp. 334S–40S; and b) Capasso, J. M., et al., "Efficacy of Angiotensin-Converting Enzyme Inhibition and $AT_1$ Receptor Blockade on Cardiac Pump Performance After Myocardial Infections in Rats", *J. Cardiovasc. Pharmacol.*, 1994, Vol. 23, pp. 584–93] and to attenuate ventricular remodeling [See Schieffer, B., et al., "Comparative Effects of Chronic Angiotensin-Converting Enzyme Inhibition and Angiotensin H Type 1 Receptor Blockade on Cardiac Remodeling After Myocardial Infarction in the Rat", *Circulation*, 1994, Vol. 89, pp. 2273–2282] in rats. In rat heart two days post-MI it has also been shown that both the left and right ventricles become more sensitive to treatment with AII resulting in reduced mechanical performance and that this negative effect can be blocked by co-administration of losartan [See Capasso, J. M., et al., "Alterations in ANG II Responsiveness in Left and Right Myocardium after Infarction-induced Heart Failure in Rats", *Am. J. Physiol.*, 1993, Vol. 264(33) pp. H2056–H2067]. Also in the rat, AII $AT_1$ receptor binding density in infarcted heart was recently shown to increase significantly as early as 3 days post-MI [See Sun, Y., et al., "Angiotensin II Receptor Binding Following Myocardial Infarction in the Rat", *Cardiovascular Research*, 1994; Vol. 28, pp. 1623–1628]. These recent experimental observations may have clinical implications as to the usefulness of losartan in the treatment of infarction induced heart failure. The importance of using a physiological preparation for the study of AII receptor antagonism should be emphasized because it has recently been shown that donor tissue from rat atria experiences an almost complete loss of $AT_2$ receptors during isolation and culturing while the expression of $AT_1$ receptors in cultured ventricular cells may be up-regulated by the culture conditions [See Feolde, E., et al., "Angiotensin II Receptor Subtypes and Biological Responses in the Rat Heart", *J. Mol. Cell. Cardiol.*, 1993, Vol. 25, pp. 1359–1367]. On the other hand, use of in vivo experimental models of myocardial ischemia to study the cardiac renin-angiotensin system (RAS) may give results in which it is difficult to differentiate the influence of the local cardiac RAS from circulating AII effects [See de Graeff, P. A., et. al., "The Cardiac Renin-Angiotensin System in Different Ischemic Syndromes of the Heart. In: Lindpaintner, K. and Ganten, D., eds. "The Cardiac-Renin Angiotensin System, Armonk, N.Y.: Futura Publishing Co., Inc., 1994, pp. 201–231].

In the present investigation the role of AII in the development of myocardial dysfunction during ischemia and reperfusion, is probed in a physiologically relevant isolated working rat heart model [See Cohen, S. M., et. al., "Simultaneous 31-P Nuclear Magnetic Resonance Spectroscopy and Mechanical Function in Working Heart Models Affected by Drugs", *Drug Dev. Res.*, 1989, Vol. 18, pp. 305–325] using the AII $AT_1$ receptor antagonist, losartan. The effects of oral pre-treatment with losartan are compared with those of placebo treatment and with losartan treatment in vitro. Observations of myocardial function are correlated with measurement of high energy phosphate metabolism and intracellular pH ($pH_i$) in the same isolated working rat hearts by continuous $^{31}P$ NMR measurements before, during, and after ischemia.

SUMMARY OF THE INVENTION

According to the present invention there is provided a method of acute treatment for enhancing functional recovery of the heart post-ischemia comprising the administration of a therapeutically effective amount of losartan, its active metabolite, EXP3174, or a pharmaceutically acceptable salt therefrom, to a patient or a patient's isolated heart in need of such treatment.

BRIEF DESCRIPTION OF THE FIGURES

FIG. 1

Figure 2B:
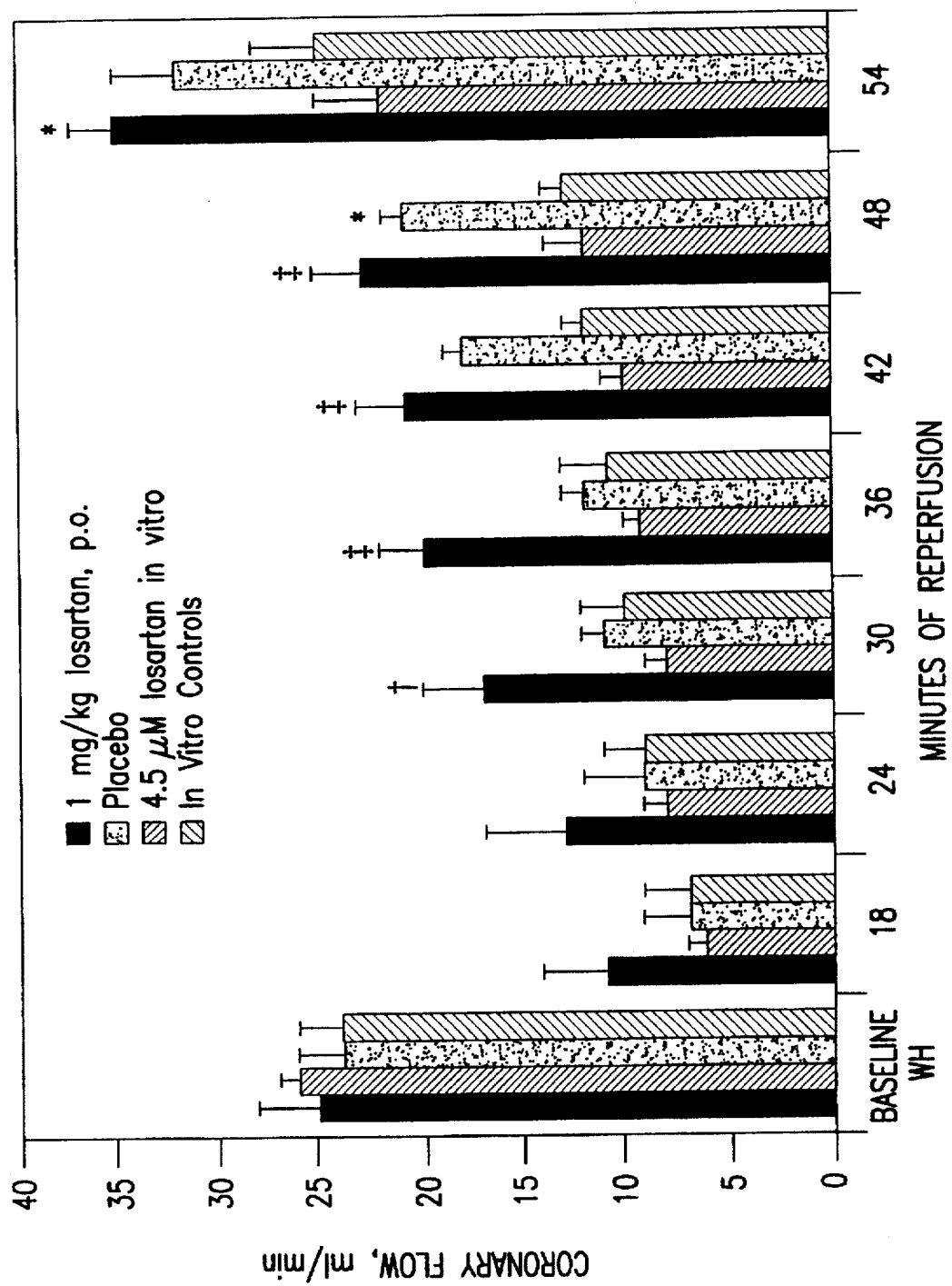

The perfusion protocol followed in all experiments.

FIG. 2

The recovery of (c) mechanical power, (b) coronary flow and (a) cardiac output following 20 minutes of global ischemia as a function of losartan treatment in vivo and in vitro [units of power are ml/min x mm Hg].

DETAILED DESCRIPTION OF THE INVENTION

The instant invention relates to a method of acute treatment for enhancing functional recovery of the heart post-ischemia comprising the administration of a therapeutically effective amount of losartan, its active metabolite, EXP3174, or a pharmaceutically acceptable salt therefrom, to a patient or a patient's isolated heart in need of such treatment.

An embodiment of this aspect of the invention is a method as described above, wherein the ischemia occurs during cardiac by-pass surgery.

A second aspect of this invention is a method of acute treatment for enhancing functional recovery of a patient's new heart post transplantation comprising the administration directly to the isolated heart during the preservation period prior to transplantation a therapeutically effective amount of losartan, its active metabolite, EXP3174, or a pharmaceutically acceptable salt therefrom.

A third aspect of this invention is the method of acute treatment of a patients partially ischemic heart prior to interventional procedures to assess or correct a coronary blockage for the purpose of enhancing subsequent functional recovery of the heart after the procedure comprising the administration to such patient of a therapeutically effective amount of losartan, its active metabolite, EXP3174, or a pharmaceutically acceptable salt therefrom.

A fourth aspect of the instant invention relates to a method of acute treatment for enhancing functional recovery after a myocardial infarction comprising the administration to a patient in need of such treatment of a therapeutically effective amount of losartan, its active metabolite, EXP3174, or a pharmaceutically acceptable salt therefrom.

Losartan and its active metabolite, EXP3174, are disclosed and claimed in US Pat. No. 5,138,069 and have the following chemical names, respectively:

2-Butyl-4-chloro-1-[(2'-tetrazol-5-yl)biphenyl-4-yl]methyl]-5-(hydroxymethyl)imidazole; and 2-Butyl-4-chloro-1-[(2'-tetrazol-5-yl)biphenyl-4-yl]methyl]-imidazole-5-carboxylic acid.

Losartan potassium salt is currently being sold in the US under the registered trademark COZAAR® for the treatment of hypertension. EXP3174 has been identified as an active metabolite of losartan potassium.

Experimental Animals and Drug Treatment

Heart donors were male Sprague-Dawley rats weighing 400–500 g and were obtained from Charles River Breeding Laboratories (Wilmington, Mass.). All animals were cared for in accordance with the Guide for the Care and Use of Laboratory Animals, NIH Publication No. 86–23, and all animal procedures were approved by our Institutional Animal Care and Use Committee. Rats were provided with chow and water ad libitum and were not fasted prior to surgery.

A total of four treatment groups were set up as follows:

(1) Losartan, in vivo, N=7: 1 mg/kg, p.o., 3.5 hours prior to excision of the heart.

(2) Placebo, in vivo, N=8: vehicle, p.o., 3.5 hours prior to excision of the heart.

(3) Losartan, in vitro, N=7: 4.5 μM added to the recirculating perfusate at least 20 minutes before ischemia.

(4) Control, in vitro, N=7: vehicle added to the recirculating perfusate at least 20 minutes before ischemia.

Losartan was administered in vivo (Group 1) as an aqueous solution by gavage, whereas placebo rats received an equivalent volume of water (Group 2). The 4.5 μM dose of losartan used in the in vitro experiments (Group 3) was chosen to insure saturation of the $AT_1$ receptor sites while remaining well below the $K_i$ of losartan for the $AT_2$ receptor subtype in heart [See Chang, R. S. L., et al., "In Vitro Pharmacology of MK-996, a New Potent and Selective Angiotensin II ($AT_1$) Receptor Antagonist", Drug Dev. Res., 1994, Vol. 32, pp. 161–171]. This dose is comparable to losartan plasma concentrations recently reported for rats receiving 1 mg/kg of the drug i.v. [See Zhuo, J., et al., "Blockade by Intravenous Losartan of $AT_1$ Angiotensin II Receptors in Rat Brain, Kidney and Adrenals Demonstrated by in vitro Autoradiography", Clinical and Experimental Pharmacology and Physiology, 1994, Vol. 21, pp.557–567], and is approximately equal to peak plasma concentrations for rats receiving 10 mg/kg orally. In orally treated rats losartan is converted into its active metabolite, EXP3174, which is almost an order of magnitude more potent than its parent compound [See Mantlo, N. B., et al., "Potent, Orally Active Imidazo[4,5-b]pyridine-based Angiotensin II Receptor Antagonists", Med. Chem., 1991, Vol. 34, pp. 2919–2922]. Consequently, the apparently high dose used here for in vitro treatment was required to provide a therapeutic effect similar to that provided by the 1 mg/kg of losartan used for in vivo dosing.

Working heart preparation

Donor rats were anesthetized with ether; 600 U/kg sodium heparin was given as an anticoagulant i.v. about two minutes prior to excision of the heart. Excised hearts were immediately placed into 50 ml of ice cold perfusion buffer for cardioplegia. Arrested hearts were then immediately perfused in Langendorff (retrograde) mode to provide adequate perfusion of the coronary vasculature while the hearts were prepared for pulmonary vein cannulation and working heart (WH) perfusion using a standard technique [See a) Neely, J. R., et al., "Effect of Pressure Development on Oxygen Consumption by Isolated Rat Heart", Am. J. Physiol., 1967, Vol. 212, pp. 804–814; b) Neely, J. R., et. al., "Techniques for Perfusing Isolated Rat Hearts: In: Hardman, J. G. and O'Malley, B. W., eds. "Methods in Enzymology, New York", Academic Press, 1975, pp.43–60; and c) Taegtmeyer, H., et al., "Utilization of Energy-Providing Substrates in the Isolated Working Rat Heart", Biochem. J., 1980, Vol. 186, pp. 701–711] with adaptations for perfusion in the NMR magnet [See Cohen, S. M., et al., Drug Dev. Res., 1989, Vol. 18, pp. 305–325]. All working heart preparations were perfused with an atrial filling pressure (AFP) of 10–11 mm Hg and a constant mean aortic pressure (MAP) of 90 mm Hg prior to ischemia as previously described [See Werrmann, J. G. et al., J. Cardiovasc. Pharmacol., 1994, Vol. 24, pp. 573–586]. A modified low-phosphate Krebs-Henseleit buffer with a pH of 7.4 after equilibration with $O_2$:$CO_2$ (95:5) at 36.2° C. was used with 15 mM glucose as sole substrate in the recirculating perfusate [See Werrmann, J. G. et al., "Comparison of the Effects of ACE Inhibition with Those of AII Receptor Antagonism on Functional and Metabolic Recovery in the Post-ischemic Working Rat Heart as Studied by $^{31}$P NMR", J. Cardiovasc. Pharmacol., 1994, Vol. 24, pp. 573–586]. Other details of the preparation were as described previously [See a) Cohen, S. M., et al., Drug Dev. Res., 1989, Vol. 18, pp. 305–325; and b) Werrmann, J. G. et al., J. Cardiovasc. Pharmacol., 1994, Vol. 24, pp. 573–586]. The perfusion protocol was identical for all treatment groups and is given in FIG. 1.

NMR Conditions

The $^{31}$P NMR spectra were measured using a Bruker AM360 wide-bore spectrometer. Each spectrum consisted of 84 to 160 scans of 60° free-induction decays with a 12 kHz window; two second recovery was allowed between pulses. Thus, each spectrum measured average metabolite levels over a 3.0 to 5.6 minute period. $^{31}$P NMR peak areas were determined with PCr and ATP quantitated as described previously [See Werrmann, J. G. et al., J. Cardiovasc. Pharmacol., 1994, Vol. 24, pp. 573–586]. The $^{31}$P NMR provided a direct measurement of intracellular pH in our isolated heart preparations. This application of $^{31}$P NMR is well established and is based on the fact that the chemical shift of intracellular inorganic phosphate is sensitive to changes in pH near its pKa of 6.8 [See Cohen, S. M., et al., Drug Dev. Res., 1989, Vol. 18, pp. 305–325].

Statistical Analysis

Differences among the treatment groups were analyzed by a one-way analysis of variance (ANOVA) followed by Tukey's multiple comparison test where indicated by the ANOVA [See Zar, J. H., Biostatistical Analysis, 2nd ed. Englewood Cliffs, N.J.: Prentice-Hall, Inc., 1984, p. 718]. All calculations and analyses were performed using the SAS software system (SAS, Cary, N.C.). All reported values are mean ±SEM.

Materials

Losartan, 2-n-butyl-4-chloro-5-hydroxymethyl-1-[(2'-(1H-tetrazole5-yl)biphenyl-4-yl)methyl]imidazole, was synthesized by Merck Research Laboratories, Rahway, N.J. All other chemicals were the highest grade available.

Recovery of hemodynamic function following global ischemia

An approximation of the mechanical power ($E_M$) of the heart is given by the sum of the pressure power ($E_P$) and kinetic power ($E_K$) of the heart [See Niesler, R. A. et al., "The Measurement of Heat Production, Mechanical Power, and Oxygen Consumption of the Isolated Working Rat Heart", Basic Res. Cardiol., 1985, Vol. 80, pp. 564–579]. The index of functional recovery used here, i.e., power, takes into account pressure work ($E_P$) and is calculated by multiplying the cardiac output (CO) by the mean developed pressure (MAP-AFP), power=CO×|MAP-AFP|. The kinetic energy expended during contraction ($E_K$), which is a relatively minor (<5%) component of the work being performed by such hearts [See a) Niesler, R. A. et al., Basic Res. Cardiol., 1985, Vol. 80, pp. 564–579; b) Kannengiesser G. J., et al., "Impaired Cardiac Work and Oxygen Uptake after Reperfusion of Regionally Ischemic Myocardium", J. Mol. Cell Cardiol., 1979, Vol. 11, pp. 197–207] is omitted from our measure of function. This approximation of the mechanical power of the heart is similar to that used by Neely, et al. and Kannengiesser, et al. [See a) Neely, J. R., et al., "Effect of Pressure Development on Oxygen Consumption by Isolated Rat Heart", Am. J. Physiol., 1967; Vol. 212, pp. 804–814; and b) Kannengiesser G. J., et al., "Impaired Cardiac Work and Oxygen Uptake after Reperfusion of Regionally Ischemic Myocardium", J. Mol. Cell Cardiol., 1979, Vol. 11, pp. 197–207], with allowances made for the preload or atrial filling pressure as in Reibel and Rovetto [See Reibel, D. K., et al., "Myocardial ATP Synthesis and Mechanical Function Following Oxygen Deficiency", Am. J. Physiol., 1978, Vol. 234(5), pp. H620–H624].

Baseline values for power, coronary flow, and cardiac output measured during working heart perfusion prior to global ischemia in this present work were essentially equal in all treatment groups studied (FIG. 2), and are comparable to baseline values measured previously under similar conditions [See Werrmann, J. G. et al., J. Cardiovasc. Pharmacol., 1994, Vol. 24, pp. 573–586]. Functional recovery from global ischemia measured for each group is summarized in Table 1. Treatment with losartan either in vivo or in vitro resulted in significantly greater recovery of function after 54 min of reperfusion (P<0.005) compared with corresponding control groups. Although the final functional recoveries measured for hearts in either of the drug treatment groups were similar, hearts from rats pre-treated with 1 mg/kg losartan demonstrated a significant improvement in function compared to the placebo group very early in the reperfusion period (ca. 24 min), whilst function did not improve significantly in hearts treated in vitro until after 42 min of reperfusion (FIG. 2).

Figure 2C:
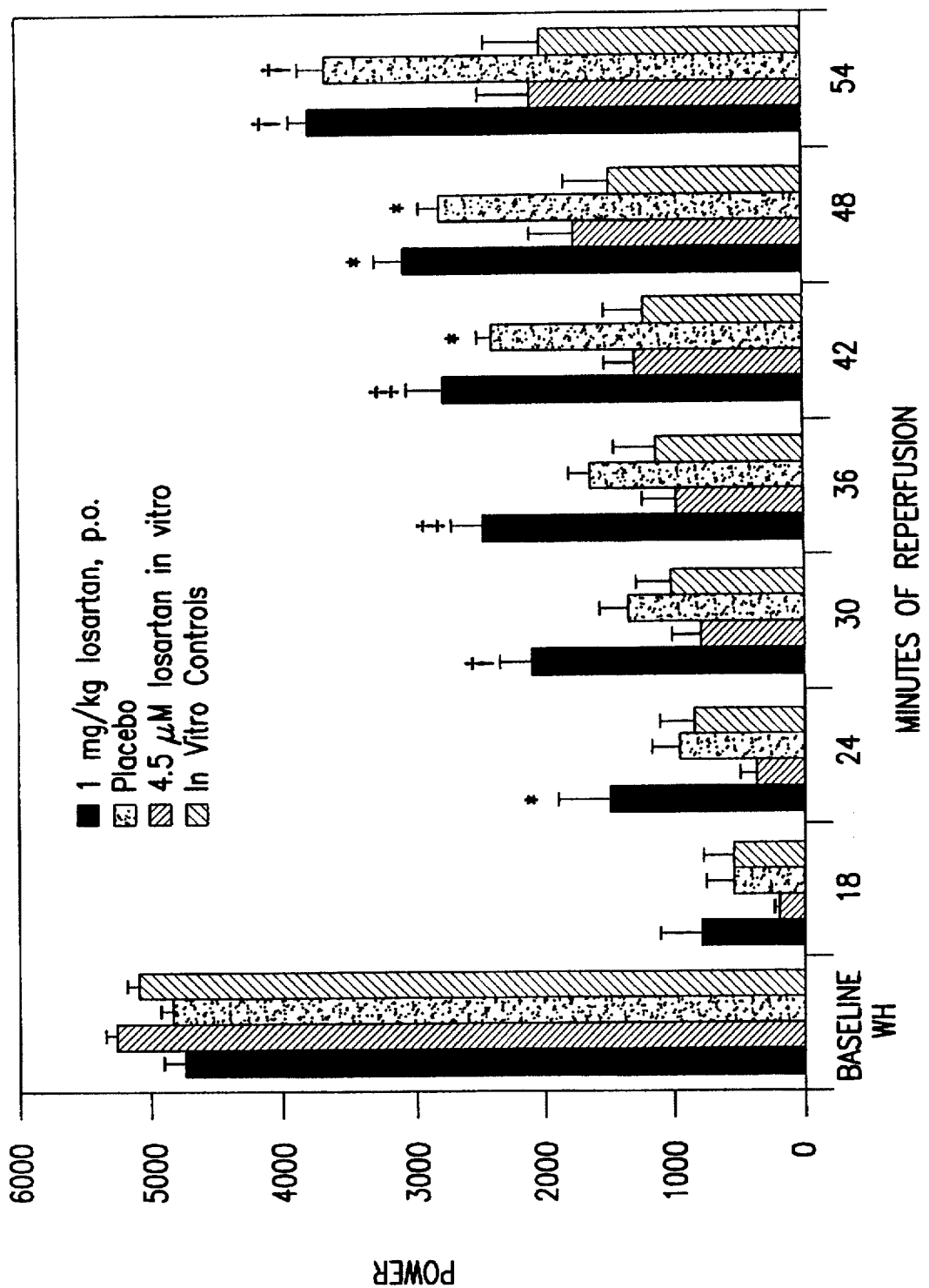

Hearts from rats treated orally with losartan demonstrated a sustained significant improvement in CF by 30 min of reperfusion that continued until the end of the reperfusion period (FIG. 2). In contrast, hearts treated with losartan in vitro showed a significant improvement in coronary flow for only one brief interval near the end of the reperfusion period.

Cardiac output was significantly greater in hearts from rats treated orally with losartan compared with the placebo group starting early in working heart reperfusion (ca. 24 min) and continuing throughout the rest of the reperfusion period (FIG. 2). Hearts treated with losartan in vitro did not achieve significant improvement in cardiac output compared with in vitro controls until after 42 min of reperfusion.

Baseline heart rates were unaffected by any of the treatment regimens. Heart rates were typically 237±4 bpm. Losartan treatment had no significant effect on the recovery of heart rate during reperfusion.

Metabolism of ATP and Phosphocreatine

Treatment with losartan either in vivo or in vitro had no effect on myocardial ATP levels before ischemia or on the changes observed in ATP levels either during or after ischemia. Baseline ATP levels were typically 24±1 µmoles/g dry weight, in agreement with the baseline levels measured in previous isolated working rat heart studies [See a) Werrmann, J. G. et al., J. Cardiovasc. Pharmacol., 1994, Vol. 24, pp. 573–586; and b) Navon, G., et al., Magn. Reson. Med., 1994, Vol. 32, pp. 556–564]. ATP levels fell to 1- to 4- µmoles/g dry weight in all treatment groups after 20 min of ischemia then recovered to 12-to 14-µmoles/g dry weight in all treatment groups after 54 min of reperfusion. Phosphocreatine levels were 23±1 to 27±1 µmol/g dry weight at baseline; drug treatment did not significantly affect the decrease in phosphocreatine levels observed during ischemia or the degree of recovery of phosphocreatine during reperfusion.

Intracellular pH

Although oral pre-treatment with losartan attenuated the development of acidosis during ischemia, this difference did not achieve significance. Pre-ischemia baseline $pH_i$ was 7.04±0.02 independent of treatment; at the end of 20 min of global ischemia, $pH_i$ fell to 6.06±0.05 in the treatment group and 5.97±0.03 in the placebo group. The recovery of $pH_i$ during reperfusion was identical for these groups. Losartan in vitro had no effect on pHi at any point in the protocol based on comparison to the in vitro controls.

To help define the contribution of the cardiac RAS to myocardial dysfunction during global ischemia and reperfusion we examined the effects of the AII $AT_1$ receptor antagonist, losartan, in isolated working heart preparations. Studying the effects of AII $AT_1$ receptor antagonism in the isolated perfused organ effectively eliminated the contribution of circulating AII and the contribution of renin-angiotensin systems located in other tissues to myocardial dysfunction during and following ischemia. In this study, AII $AT_1$ receptor antagonism resulted a in significantly improved myocardial function during reperfusion following 20 minutes of global ischemia. A functional recovery of 79±3% (Table 1) was measured in hearts from rats treated in vivo with losartan at a 1 mg/kg dose level. Hearts treated with 4.5 µM losartan in vitro showed about a 75±4% recovery of mechanical function (Table 1). In orally treated rats the binding affinity of losartan was most likely attributed in part to the conversion of losartan into its active metabolite, EXP3174, which has an 8-fold greater binding affinity than losartan [See Mantlo, N. B., et al., J. Med. Chem., 1991, Vol. 34, pp. 2919–2922]. Thus, for both the in vivo and in vitro treatment conditions, the correlation of the effective in vitro binding affinities of this AII $AT_1$ antagonist with the resulting improvement in functional recovery following ischemia is consistent with the protective effects exerted by this compound being the result of specific antagonism of the $AT_1$ receptor.

TABLE 1

The effect of AII (AT$_1$) receptor antagonist treatment on functional recovery in isolated working rat hearts following 20 minutes of ischemia.

| Group | No. of hearts | Functional recovery* (%) | Significance level vs. corresponding control |
|---|---|---|---|
| Treatment in vivo | | | |
| Losartan, 1 mg/kg, p.o. | 7 | 80 ± 4% | P < 0.05 |
| Placebo, vehicle, p.o. | 8 | 39 ± 8% | |
| Treatment in vitro | | | |
| Losartan, 4.5 µM in vitro | 7 | 75 ± 4% | P < 0.005 |
| Control, vehicle in vitro | 7 | 38 ± 9% | |

*Functional Recovery = [power$_{final}$/power$_{initial}$] × 100. All values are mean ± SEM.

During reperfusion following ischemia, both coronary flow and cardiac output were significantly improved with losartan treatment. The diminished myocardial dysfunction resulting from AII to AT$_1$ receptor antagonireceptor antagonism was essentially independent of high energy phosphate metabolism with losartan treatment as reflected in the levels of ATP and phosphocreatine. The effects observed with losartan were consistent with the findings made with 7-methyl-2-propyl-3-[2'-(5-tetrazoly)-1,1'-biphenyl-4-yl)methyl]-3H-imidazo[4,5-b]pyridine, hereinafter referred to as Compound A, another structurally distinct AII AT$_1$ receptor antagonist, and may thus be characteristic of this class of compounds [See Werrmann, J. G., et al., "Comparison of the Effects of ACE Inhibition with Those of AII Receptor Antagonism on Functional and Metabolic Recovery in the Post-ischemic Working Rat Heart as Studied by $^{31}$P NMR", J. Cardiovasc. Pharmacol., 1994, Vol. 24, pp. 573–586]. The only significant effect that was specific to one of these AII antagonists related to the development of acidosis during ischemia. Oral pre-treatment with Compound A resulted in significant attenuation in the development of acidosis in the myocardium during ischemia compared to treatment with placebo, whereas oral pre-treatment with losartan had a moderate but non-significant effect on the development of acidosis during cardiac ischemia compared with placebo treatment. Although the effect of AII antagonism on pH$_i$ during ischemia appears to be specific for Compound A and may not be observed with AII antagonist treatment in general, the failure of losartan to attenuate the development of acidosis significantly did not diminish its protective effects on myocardial function as compared to Compound A.

The faster recovery of hemodynamic function exhibited by the losartan in vivo group compared with the losartan in vitro group (FIG. 2) might have been due to the longer period of exposure of the myocardium to the drug in the orally pre-treated group compared with the 20 minute exposure period to the drug experienced by the in vitro group prior to ischemia. The faster recovery demonstrated by the orally pre-treated group is consistent with a reduction in myocardial stunning following the short period of ischemia used in this study; however, the exact mechanism responsible for this effect is obscure. A factor to be considered with in vivo treatment is the metabolism of losartan to its more potent active metabolite, EXP3174. The delay in the beneficial impact of losartan in vitro may possibly be related to the absence of EXP3174 under this condition. It should be emphasized that although the group orally pre-treated with losartan recovered hemodynamic function faster than the group treated with losartan in vitro, the final recovery experienced by each of the drug-treated groups at the end of the 54 minute reperfusion period was essentially the same. Therefore, differences in functional recovery between the modes of treatment employed relate only to the rate of recovery from ischemia and not to the total recovery obtained.

The present observations with losartan also agree with the results from our earlier study in which treatment with the ACE inhibitor, lisinopril in vivo resulted in reduced myocardial damage following ischemia in the isolated perfused heart [See Werrmnann, J. G. et al., J. Cardiovasc. Pharmacol., 1994, Vol. 24, pp. 573–586]. Others have reported similar protective effects with ACE inhibitor treatment in their isolated perfused heart models [See a) Cohen, S. M., et al., Drug Dev. Res., 1989, Vol. 18, pp. 305–325; b) Linz, W., et al., "Beneficial Effects of the Converting Enzyme Inhibitor, Ramapril, in Ischemic Rat Hearts", J. Cardiovasc. Pharmacol., 1986, Vol. 8(Suppl. 10), pp. S91–S99; c) Li, K., et al., "Protective Effects of Captopril and Enalapril on Myocardial Ischemia and Reperfusion Damage of Rat", J. Mol. Cell. Cardiol., 1987, Vol. 19, pp. 909–915; d) Linz, W., et al., "Local Inhibition of Bradykinin Degradation in Ischemic Hearts", J. Cardiovasc. Pharmacol., 1990, Vol. 15(Suppl 6), pp. S99–S109; and e) Liu, X., et al., "Attenuation of Myocardial Reperfusion Injury by Sulfhydryl-containing Angiotensin Converting Enzyme Inhibitors", Cardiovasc. Drugs Ther., 1992, Vol., pp. 437–4431]. In contrast to the significant improvement in myocardial performance measured during reperfusion in hearts treated with either AII AT$_1$ receptor antagonist in vitro, lisinopril treatment in vitro did not reduce myocardial injury [See Werrmann, J. G. et al., J. Cardiovasc. Pharmacol., 1994, Vol. 24, pp. 573–5861]. Although tissue AII levels were not measured, one can speculate that lack of an acute effect of ACE inhibitor treatment in vitro in our isolated heart model may be due to incomplete washout of endogenous tissue AII subsequent to ACE inhibition and prior to the ischemic insult. It is possible that AII AT$_1$ receptor antagonists will prove useful in the acute treatment of myocardial infarction because they act directly at the receptor level, thus providing a rapid mechanism for blocking the effects of AII.

The present findings are consistent with the suggestion that a reduction in the stimulation of the AT$_1$ AII receptor, secondary to reduced AII levels may be the dominant cardioprotective mechanism of ACE inhibitors.

Another possible mechanism whereby AT$_1$ receptor antagonism by losartan may reduce myocardial dysfunction during ischemia and reperfusion under our conditions resides in an attenuation of the increase in intracellular sodium and, subsequently, calcium (through Na/Ca exchange) that takes place during ischemia and reperfusion. We have recently shown [See Navon, G., et al., "$^{31}$P NMR and Triple Quantum Filtered $^{23}$Na NMR Studies of the Effects of Inhibition of Na$^+$/H$^+$Exchange on Intracellular Sodium and pH in Working and Ischemic Hearts", Magn. Reson. Med., 1994, Vol. 32, pp. 556–5641 that under these same experimental conditions intracellular sodium levels [Na$_i$] increase substantially during ischemia and in the early stages of reperfusion, and that this increase in [Na$_i$] is significantly attenuated by the Na$^+$/H$^+$ antiporter inhibitor EIPA, (N-ethyl-N-isopropyl)amiloride. Inhibition of Na$^+$/H$^+$ exchange resulted in significantly improved recovery of mechanical function following ischemia and reperfusion in EIPA-treated hearts compared with control hearts. Stimulation of Na$^+$/H$^+$ exchange in rabbit ventricular myocytes by angiotensin II has been reported recently [See Matsui, H., et al., "Angiotensin II Stimulates Sodium-hydrogen Exchange in Adult Rabbit Ventricular Myocytes", *Cardiovasc. Res.*, 1995, Vol. 29, pp. 215–221]. Stimulation of $Na^+/H^+$ exchange by angiotensin II was also demonstrated in OKP cells [See Cano, A., et al., "Angiotensin II Stimulation of Na-H Antiporter Activity is cAMP Independent in OKP Cells", *Am. J. Physiol.*, 1994, Vol. 266 (Cell Physiol 35), pp. C1603–C1608], an opossum kidney cell line, where is was further shown by use of losartan that this effect was mediated by an $AT_1$ receptor coupled mechanism.

This study reports the initial observation of a significant reduction in myocardial dysfunction during reperfusion following 20 minutes of global ischemia in the isolated perfused heart as a result of acute AII $AT_1$ receptor antagonism by losartan. Diminished myocardial dysfunction in treated hearts was characterized by an improvement in the recovery of CF and CO that was both highly significant (P<0.005) and independent of high-energy phosphate metabolism. Losartan treatment did not have a significant effect on the development of acidosis during ischemia or on the recovery of intracellular pH during reperfusion. Overall, the results from this isolated working heart study give further demonstration of the integral role of the cardiac RAS in the development of myocardial dysfunction during ischemia and reperfusion. The use of potent specific AII receptor antagonists in studies of isolated perfused hearts provides a versatile approach for highlighting the physiological significance of the local cardiac RAS in myocardial ischemia.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. The preferred salts of this invention include, but are not limited to: potassium, sodium, calcium and ammonium salts of losartan and its active metabolite, EXP3174.

Included within the scope of this invention is a method of treatment of as recited above using pharmaceutical compositions comprising losartan, its active metabolite, EXP3174 or a pharmaceutically acceptable salt therefrom and a suitable pharmaceutical carrier.

DOSAGE FORMS

The pharmaceutical compositions of this invention can be administered for this method of treatment by any means that effects contact of the active ingredient compound with the site of action. For example, administration, can be parenteral, i.e., subcutaneous, intravenous, intramuscular or intra peritoneal. Alternatively, or concurrently in some cases administration can be by the oral route.

The pharmaceutical compositions of this invention can be administered by any conventional means available for use in conjunction with pharmaceuticals. The pharmaceutical compositions can be administered alone, but are generally administered with a pharmaceutical carrier selected on the basis of the chosen route of administration and standard pharmaceutical practice.

For the purpose of this disclosure, the term patient is defined as a mammal, preferably human.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results.

The active ingredients can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of losartan or EXP3174 for this invention can be illustrated as follows:

CAPSULES

A large number of unit capsules are prepared by filling standard two-piece hard gelatin capsules each with a pharmacologically appropriate amount in milligrams of the powdered active ingredients, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing a pharmacologically appropriate amount in milligrams of the active ingredient. The capsules are washed and dried.

TABLETS

A large number of tablets are prepared by conventional procedures so that the dosage unit is a pharmacologically appropriate amount in milligrams of the active ingredients, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring a pharmacologically appropriate amount by weight of the active ingredients in 10% by volume propylene glycol. The solution is made to volume with water for injection and sterilized.

SUSPENSION

An aqueous suspension is prepared for oral administration so that each 5 milliliters contain a pharmacologically appropriate amount in milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The above dosage forms and routes of administration will depend upon the method of treatment. If the method of treatment is to enhance the functional recovery of the isolated heart during transplantation or while the heart is on by pass, then the route of administration will be via the direct addition to the preservation solution that is typically employed during a transplant procedure or addition to the heart while it is on by-pass. Additionally, the method of treatment may require the administration of losartan or EXP3174 to the patient by one of the traditional routes outlined above.

What is claimed is:

1. A method of acute treatment for enhancing functional recovery of a heart post-ischemia comprising the administration of a single dose of a therapeutically effective amount of losartan, EXP3174, or a pharmaceutically acceptable salt of either compound, to a patient or a patient's isolated heart in need of said treatment.

2. The method as described in claim 1, wherein the ischemia occurs during cardiac by-pass surgery.

3. A method of acute treatment for enhancing functional recovery of a patient's new heart post transplantation comprising the administration directly to the isolated heart during the preservation period prior to transplantation a single dose of a therapeutically effective amount of losartan, EXP3174, or a pharmaceutically acceptable salt of either compound.

4. A method of acute treatment for enhancing functional recovery after a myocardial infarction comprising the administration to a patient in need of said treatment of a single dose of a therapeutically effective amount of losartan, EXP3174, or a pharmaceutically acceptable salt of either compound.

5. A method of treatment of a patient's partially ischemic heart prior to an interventional procedure, where said interventional procedure is undertaken to assess or correct a coronary blockage, comprising the administration to said patient of a single dose of a therapeutically effective amount of losartan, EXP3174, or a pharmaceutically acceptable salt of either compound for the purpose of enhancing subsequent functional recovery of the heart after the interventional procedure.

* * * * *

UNITED STATES PATENT AND TRADEMARK OFFICE
CERTIFICATE OF CORRECTION

PATENT NO.  : 5,795,904
DATED       : August 18, 1998
INVENTOR(S) : Cohen et al.

It is certified that error appears in the above-identified patent and that said Letters Patent is hereby corrected as shown below:

On the title page, and Col 1;
In [54] please correct TITLE it should read -

ENHANCED FUNCTIONAL RECOVERY OF THE HEART BY LOSARTAN TREATMENT AFTER AN ISCHEMIC ATTACK

Signed and Sealed this

Twelfth Day of January, 1999

Attest:

Attesting Officer

*Acting Commissioner of Patents and Trademarks*